(12) United States Patent
Wang et al.

(10) Patent No.: US 9,304,076 B2
(45) Date of Patent: Apr. 5, 2016

(54) CLEANING EQUIPMENT OF SAMPLE BOTTLE FOR CHROMATOGRAPHY ANALYSIS AND CLEANING METHOD THEREOF

(71) Applicant: Shenzhen China Star Optoelectronics Technology Co., Ltd., Shenzhen, Guangdong (CN)

(72) Inventors: Li Wang, Shenzhen (CN); Jingming Wu, Shenzhen (CN); Hongqing Huang, Shenzhen (CN); Weiwei Zhang, Shenzhen (CN); Rui Xu, Shenzhen (CN); Xiaobo He, Shenzhen (CN); Honghui Zhu, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 504 days.

(21) Appl. No.: 13/979,672

(22) PCT Filed: Jun. 21, 2013

(86) PCT No.: PCT/CN2013/077680
§ 371 (c)(1),
(2) Date: Jul. 15, 2013

(87) PCT Pub. No.: WO2014/180026
PCT Pub. Date: Nov. 13, 2014

(65) Prior Publication Data
US 2014/0326279 A1  Nov. 6, 2014

(30) Foreign Application Priority Data
May 6, 2013  (CN) .......................... 2013 1 0162068

(51) Int. Cl.
*G01N 21/11* (2006.01)
*B08B 3/10* (2006.01)

(52) U.S. Cl.
CPC  *G01N 21/11* (2013.01); *B08B 3/10* (2013.01); *G01N 2021/115* (2013.01)

(58) Field of Classification Search
CPC .. G01N 2021/115; G01N 21/11; G01N 21/13
See application file for complete search history.

(56) References Cited

U.S. PATENT DOCUMENTS

2008/0285025 A1* 11/2008 Adachi ..................... G01J 3/02
356/300

\* cited by examiner

*Primary Examiner* — Jason Ko
(74) *Attorney, Agent, or Firm* — Andrew C. Cheng

(57) ABSTRACT

A cleaning equipment of sample bottle for chromatography analysis comprising: a base; a support frame vertically fixed to the base; a horizontal column having two ends, wherein one of the ends is disposed at the support frame through an adjustment knob; a rotary drive device fixed to the other end of the horizontal columns; a rotation disk which can rotate through driving of the rotary drive device, and a side edge of the rotation disk provides with multiple placing holes for receiving and fixing sample bottles; a cleaning agent recycling tank disposed below the rotation disk, wherein a side wall of it provides with an ejector pipe connected with a water pump; and a control unit for controlling on/off and rotation speed of the rotary drive device, and on/off of the water pump. The invention also provides a cleaning method of sample bottle for chromatography analysis.

11 Claims, 1 Drawing Sheet

CLEANING EQUIPMENT OF SAMPLE BOTTLE FOR CHROMATOGRAPHY ANALYSIS AND CLEANING METHOD THEREOF

The claims of this application have submitted to the State Intellectual Property Office of the People's Republic of China (SIPO) on May 6, 2013, Application No. 201310162068.5. The priority right based on the China application has a title of "A cleaning equipment, and more particularly to a cleaning equipment of sample bottle for chromatography analysis and a cleaning method thereof". The entire contents of the above-mentioned patent application will be incorporated in the present application through citing.

BACKGROUND OF THE INVENTION

1. Field of the Invention

The present invention relates to a cleaning equipment, and more particularly to a cleaning equipment of sample bottle for chromatography analysis and a cleaning method thereof.

2. Description of Related Art

High Performance Liquid Chromatography (HPLC) analysis method and gas chromatography (GC) analysis method are two major branches of the chromatography analysis method, and they are widely used in environmental monitoring, pharmacy, medicine, and TFT-LCD industry etc., for example, in TFT-LCD industry, when analyzing liquid crystal, stripping liquid, or photoresist, it will often use those chromatography analysis methods.

The analysis equipment used by the HPLC and GC analysis methods can be divided into a sample entering system, a separation system and a detection system. Wherein, the sample entering system will use an auto sample entering device. The auto sample entering device has great convenience for the batch processing such that it greatly improves the analysis efficiency and saves labor costs. However, the treatment of a large number of the consumed sample bottles also will become a problem at the same time. The sample bottles are the small-diameter container, and they are difficult to clean so that they are often the single use items. Therefore, it increases consumables costs in a certain degree and also causes the waste of resources.

The HPLC and GC analysis methods will consume a large number of sample bottles at the batch processing. The sample bottles are made of glass, and they generally belong to reusable consumables. However, because of small-diameter, it does not have a mature cleaning method for the sample bottles currently. If it uses the traditional cleaning method by labor using brush, it will produce a great amount of work, and the sample bottles are not easy to clean so as to affect the effects of secondary use. In order to avoid cross-contamination between samples, many laboratories utilize single-use sample bottle. It increases consumables costs and also causes the waste of resources by this method.

SUMMARY OF THE INVENTION

The technical problem solved by the present invention is to provide a cleaning equipment having simple structure for sample bottles and a cleaning method thereof. It can clean the sample bottles easily and cleanly after chromatography analysis in order to achieve the purpose of recycling and saves the cost of equipment consumables.

In order to solve the above-mentioned technical problem, a technical solution provided by the present invention is a cleaning equipment of sample bottle for chromatography analysis comprising: a base; a support frame vertically fixed to the base; a horizontal column having two ends, wherein one of the ends is disposed at the support frame through an adjustment knob to allow the horizontal column to moves up and down along the support frame; a rotary drive device fixed to the other end of the horizontal columns; a rotation disk connected to the rotary drive device through a rotation shaft and located below the rotary drive device, wherein the rotation disk can rotate at different rotation speeds through driving of the rotary drive device, and a side edge of the rotation disk provides with a plurality of placing holes for receiving and fixing sample bottles waited for cleaning; a cleaning agent recycling tank disposed below the rotation disk, wherein a side wall of the cleaning agent recycling tank provides with an ejector pipe, and the ejector pipe connects with a water pump for ejecting cleaning agent from at least one cleaning tank to the cleaning agent recycling tank; and at least one control unit for controlling on/off and rotation speed of the rotary drive device, on/off of the water pump, and ejection speed and duration time of the cleaning agent.

Wherein, the at least one cleaning tank comprises two cleaning tanks, and the cleaning tanks communicate with the water pump through a pipe, and the pipe is provided with a valve for switching.

Wherein, each of the placing holes of the rotation disk is provided with a fixing knob running through a side wall of each of the placing holes for fixing the sample bottles waited for cleaning to the placing holes.

Wherein the placing holes disposed at the side edge of the rotation disk have multiple specifications.

Wherein, the cleaning agent recycling tank is disposed above the base.

Wherein, a bottom of the cleaning agent recycling tank provides with a liquid outlet.

Correspondingly, another embodiment of the present invention provides a cleaning equipment of sample bottle for chromatography analysis comprising:

a base; a support frame vertically fixed to the base; a horizontal column having two ends, wherein one of the ends is disposed at the support frame through an adjustment knob to allow the horizontal column to moves up and down along the support frame; a rotary drive device fixed to the other end of the horizontal columns; a rotation disk connected to the rotary drive device through a rotation shaft and located below the rotary drive device, wherein the rotation disk can rotate at different rotation speeds through driving of the rotary drive device, and a side edge of the rotation disk provides with a plurality of placing holes for receiving and fixing sample bottles waited for cleaning, wherein each of the placing holes of the rotation disk is provided with a fixing knob running through a side wall of each of the placing holes for fixing the sample bottles waited for cleaning to the placing holes; a cleaning agent recycling tank disposed below the rotation disk, wherein a side wall of the cleaning agent recycling tank provides with an ejector pipe, and the ejector pipe connects with a water pump for ejecting cleaning agent from at least one cleaning tank to the cleaning agent recycling tank; and at least one control unit for controlling on/off and rotation speed of the rotary drive device, on/off of the water pump, and ejection speed and duration time of the cleaning agent.

Wherein, the at least one cleaning tank comprises two cleaning tanks, and the cleaning tanks communicate with the water pump through a pipe, and the pipe is provided with a valve for switching.

Wherein, the placing holes disposed at the side edge of the rotation disk have multiple specifications.

Wherein, the cleaning agent recycling tank is disposed above the base.

Wherein, a bottom of the cleaning agent recycling tank provides with a liquid outlet.

Correspondingly, another embodiment of the present invention provides a cleaning method of sample bottle for chromatography analysis comprising:

disposing sample bottles waited for cleaning into placing holes of a rotation disk, and adjusting fixing knobs on the rotation disk to sequentially clamp the sample bottles waited for cleaning, wherein after clamping, outlets of the sample bottles are outward horizontally;

adjusting a position of a rotary drive device on a support frame such that the rotation disk disposed with the sample bottles descends into a cleaning agent recycling tank, and make the outlets of the sample bottles locate at the same level with an ejector pipe;

driving the rotary drive device to drive the rotation disk to rotate at a first rotation speed;

turning on a water pump and a predetermined cleaning process such that a cleaning agent in a cleaning tank ejects from the ejector pipe at a second speed and injects into each of the sample bottles waited for cleaning under rotating, and continuing for a predetermined cleaning time; and after the predetermined cleaning process, turning off the water pump and adjusting an adjusting knob such that the rotary drive device on the support frame ascends to a suitable height, and removing cleaned sample bottles from the rotation disk.

Wherein, after the predetermined cleaning process, further comprises a step of turning off the water pump and adjusting the rotation speed of the rotary drive device such that the rotation disk rotates at a third rotation speed for throwing out a residual cleaning agent in the sample bottles.

Wherein, the third rotation rate is greater than the first rotation speed.

Wherein, further comprises a step of placing the cleaned sample bottles in an oven for drying.

According to embodiments of the present invention, they provide a cleaning equipment and method of sample bottle for chromatography analysis. The cleaning equipment is simple in structure, easy to produce, easy to operate so as to be convenient for cleaning the sample bottle having small diameter, to improve cleaning efficiency, and to save the costs of the equipment consumables.

BRIEF DESCRIPTION OF THE DRAWINGS

In order to more clearly illustrate the technical solution in the present invention or in the prior art, the following will illustrate the figures used for describing the embodiments or the prior art. It is obvious that the following figures are only some embodiments of the present invention. For the skilled persons of ordinary skill in the art without creative effort, it can also obtain other figures according to these figures.

DETAILED DESCRIPTION OF THE PREFERRED EMBODIMENT

The following content combines with the drawings and the embodiment for describing the present invention in detail.

Figure 1:
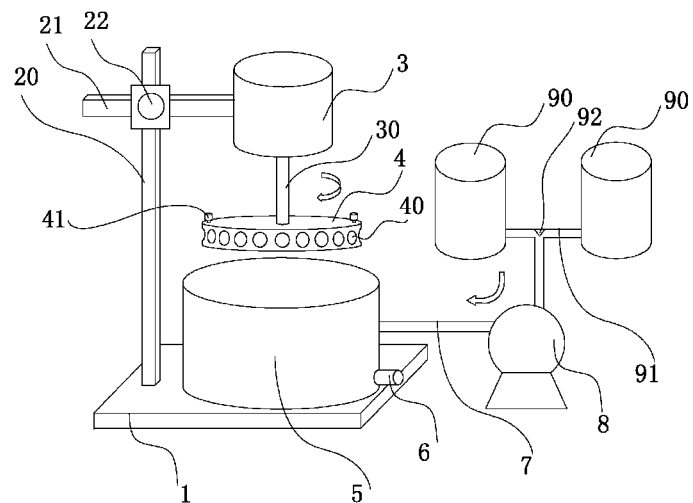
FIG. 1 is a schematic view illustrating a cleaning equipment of sample bottle for chromatography analysis according to an embodiment of the present invention.
Figure 2:
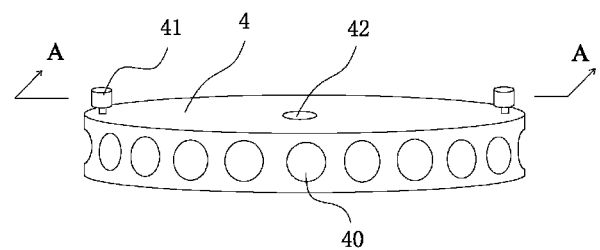
FIG. 2 is a schematic view illustrating a rotation disk according to an embodiment of the present invention.
Figure 3:
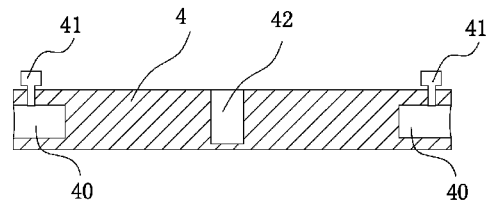
FIG. 3 is a sectional view of A-A line shown in FIG. 2.

With reference to FIG. 1 to FIG. 3, a cleaning equipment for chromatography sample bottle of the present invention comprises a base 1, a support frame 20, a horizontal column 21, an adjusting knob 22, a rotary drive device 3, rotation shaft 30, rotation disk 4, and a cleaning agent recycling tank 5.

The base 1 is for supporting or fixing the cleaning equipment. The support frame 20 is vertically fixed to the base 1 and has a column shape. The horizontal column 21 having two ends, wherein one of the ends is disposed at the support frame 20 through the adjustment knob 22. Through the adjustment knob 22, it will allow the horizontal column 21 to moves up and down along the support frame 20, and the other end of the horizontal column 21 is fixed to the rotary drive device 3;

The rotation disk 4 has a disc shape and is connected to and located below the rotary drive device 3 through the rotation shaft 30. The rotation disk 4 can rotate at different rotation speeds through the driving of the rotary drive device 3. A side edge of the rotation disk 4 provides with a plurality of placing holes 40 for receiving and fixing sample bottles waited for cleaning. The rotation shaft 30 is fixed to a blind hole 42 located at a center of the rotation disk 4.

Each of the placing holes 40 is provided with a fixing knob 41 running through a side wall (e.g., upper side wall) of the placing hole 40 for fixing the sample bottle waited for cleaning to the placing hole 40. In the actual application, the fixing knob 41 and the side wall can utilize a matching method as screw thread. FIG. 2 shows two fixing knob 41, which is only for the convenience of the drawing. In another embodiment, each of the placing holes 40 corresponds to one fixing knob 41.

The cleaning agent recycling tank 5 is disposed below the rotation disk 4 and above the base 1. A side wall of the cleaning agent recycling tank 5 provides with an ejector pipe 7. The ejector pipe 7 connected with a water pump 8 for ejecting cleaning agent from a cleaning tank 90 to the cleaning agent recycling tank 5. In FIG. 1, the number of the cleaning tank 90 is two, which can contain different cleaning agents with different concentrations or components to communicate with the water pump 8 through a pipe 91. The pipe 91 is provided with a valve 92 for switching. It should be understood that in another embodiment, it can also provide with one cleaning tank 90, and the cleaning agent recycling tank 5 provides with a liquid outlet 6 at bottom position.

Furthermore, the cleaning equipment for chromatography sample bottle of the present invention comprises at least one control unit (not shown) for controlling the on/off and rotation speed of the rotary drive device 3. The at least one control unit can also control the on/off, ejection speed of the cleaning agents, and the duration of the water pump 8. In the actual application, it can utilize the industry controller such as the programmable logic device PLC to control. It can be understood that the above features can be integrated in an industrial controller to be implemented, or may be separately controlled by a plurality of industrial controllers.

Furthermore, in a specific embodiment, it can provide with the placing holes 40 having multiple specifications according to the size (diameter) of the sample bottle waited for cleaning. For example, it can provide with the placing holes 40 having two or three specifications at the side wall of the rotation disk 4.

The present invention also provides a cleaning method of sample bottle for chromatography analysis comprises the following steps.

Adjusting a position of a rotary drive device 3 on a support frame 20 such that a rotation disk 4 locates above a cleaning agent recycling tank 5, and make sample bottle easily dispose into the rotation disk 4.

Disposing the sample bottles waited for cleaning into the placing holes 40 of the rotation disk 4, and adjusting fixing knobs 41 on the rotation disk 4 to sequentially clamp the sample bottles waited for cleaning, wherein after clamping, outlets of the sample bottles are outward horizontally.

Adjusting the position of the rotary drive device 3 on the support frame 20 again such that the rotation disk 4 disposed with the sample bottles descends into a cleaning agent recycling tank 5, and makes outlets of the sample bottles locate at the same level with an ejector pipe 7.

Driving the rotary drive device 3 to drive the rotation disk 4 to rotate at a first rotation speed; turning on a water pump 8 and a predetermined cleaning process such that cleaning agent in the cleaning tank 9 ejects from the ejector pipe 7 at a second speed according to a certain program and injects into each of the sample bottles waited for cleaning under rotating. Therefore, by utilizing the centrifugal force under rotating, the cleaning agent flows in the sample bottles and is thrown out. After continuing for a predetermined cleaning time, it can clean the sample bottles, and the waste cleaning agent can be discharged at the liquid outlet 6.

After the cleaning process, turning off the water pump 8 and adjusting the rotation speed of the rotary drive device 3 such that the rotation disk 4 rotates at a third rotation speed for throwing out residual cleaning agent in the sample bottles. To achieve a better effect, the third rotation rate is generally greater than the first rotation speed. It adjusts the adjusting knob 22 such that the rotary drive device 3 on the support frame 20 ascends to a suitable height, and removing the cleaned sample bottles from the rotation disk 4. It places the cleaned sample bottle in an oven to for drying at an appropriate temperature.

Implementing the embodiments of the present invention has the following beneficial effects: according to embodiments of the present invention, they provide a cleaning equipment and method of sample bottle for chromatography analysis. The cleaning equipment is simple in structure, easy to produce, easy to operate so as to be convenient for cleaning the sample bottle having small diameter, to improve cleaning efficiency, and to save the costs of the equipment consumables.

The above embodiments of the present invention are not used to limit the claims of this invention. Any use of the content in the specification or in the drawings of the present invention which produces equivalent structures or equivalent processes, or directly or indirectly used in other related technical fields is still covered by the claims in the present invention.

What is claimed is:

1. A cleaning equipment of sample bottle for chromatography analysis comprising:
    a base;
    a support frame vertically fixed to the base;
    a horizontal column having two ends, wherein one of the ends is disposed at the support frame through an adjustment knob to allow the horizontal column to moves up and down along the support frame;
    a rotary drive device fixed to the other end of the horizontal columns;
    a rotation disk connected to the rotary drive device through a rotation shaft and located below the rotary drive device, wherein the rotation disk can rotate at different rotation speeds through driving of the rotary drive device, and a side edge of the rotation disk provides with a plurality of placing holes for receiving and fixing sample bottles waited for cleaning;
    a cleaning agent recycling tank disposed below the rotation disk, wherein a side wall of the cleaning agent recycling tank provides with an ejector pipe, and the ejector pipe connects with a water pump for ejecting cleaning agent from at least one cleaning tank to the cleaning agent recycling tank; and
    at least one control unit for controlling on/off and rotation speed of the rotary drive device, on/off of the water pump, and ejection speed and duration time of the cleaning agent.

2. The cleaning equipment of sample bottle for chromatography analysis according to claim 1, wherein, the at least one cleaning tank comprises two cleaning tanks, and the cleaning tanks communicate with the water pump through a pipe, and the pipe is provided with a valve for switching.

3. The cleaning equipment of sample bottle for chromatography analysis according to claim 1, wherein each of the placing holes of the rotation disk is provided with a fixing knob running through a side wall of each of the placing holes for fixing the sample bottles waited for cleaning to the placing holes.

4. The cleaning equipment of sample bottle for chromatography analysis according to claim 3, wherein the placing holes disposed at the side edge of the rotation disk have multiple specifications.

5. The cleaning equipment of sample bottle for chromatography analysis according to claim 4, wherein the cleaning agent recycling tank is disposed above the base.

6. The cleaning equipment of sample bottle for chromatography analysis according to claim 5, wherein a bottom of the cleaning agent recycling tank provides with a liquid outlet.

7. A cleaning equipment of sample bottle for chromatography analysis comprising:
    a base;
    a support frame vertically fixed to the base;
    a horizontal column having two ends, wherein one of the ends is disposed at the support frame through an adjustment knob to allow the horizontal column to moves up and down along the support frame;
    a rotary drive device fixed to the other end of the horizontal columns;
    a rotation disk connected to the rotary drive device through a rotation shaft and located below the rotary drive device, wherein the rotation disk can rotate at different rotation speeds through driving of the rotary drive device, and a side edge of the rotation disk provides with a plurality of placing holes for receiving and fixing sample bottles waited for cleaning, wherein each of the placing holes of the rotation disk is provided with a fixing knob running through a side wall of each of the placing holes for fixing the sample bottles waited for cleaning to the placing holes;
    a cleaning agent recycling tank disposed below the rotation disk, wherein a side wall of the cleaning agent recycling tank provides with an ejector pipe, and the ejector pipe connects with a water pump for ejecting cleaning agent from at least one cleaning tank to the cleaning agent recycling tank; and
    at least one control unit for controlling on/off and rotation speed of the rotary drive device, on/off of the water pump, and ejection speed and duration time of the cleaning agent.

8. The cleaning equipment of sample bottle for chromatography analysis according to claim 7, wherein the at least one cleaning tank comprises two cleaning tanks, and the cleaning tanks communicate with the water pump through a pipe, and the pipe is provided with a valve for switching.

9. The cleaning equipment of sample bottle for chromatography analysis according to claim 8, wherein the placing holes disposed at the side edge of the rotation disk have multiple specifications.

10. The cleaning equipment of sample bottle for chromatography analysis according to claim 9, wherein the cleaning agent recycling tank is disposed above the base.

11. The cleaning equipment of sample bottle for chromatography analysis according to claim 10, wherein a bottom of the cleaning agent recycling tank provides with a liquid outlet.

* * * * *